(12) United States Patent
Leppard et al.

(10) Patent No.: US 7,214,830 B2
(45) Date of Patent: May 8, 2007

(54) PROCESS FOR THE PREPARATION OF ACYLPHOSPHINES, ACYL OXIDES AND ACYL SULFIDES

(75) Inventors: David George Leppard, Marly (CH); Eugen Eichenberger, Basel (CH); René Kaeser, Rechthalten (CH); Gebhard Hug, Rheinfelden (CH); Urs Schwendimann, Baleares Mallorca (ES)

(73) Assignee: Ciba Specialty Chemicals Corporation, Tarrytown, NY (US)

( * ) Notice: Subject to any disclaimer, the term of this patent is extended or adjusted under 35 U.S.C. 154(b) by 0 days.

(21) Appl. No.: 11/348,042

(22) Filed: Feb. 6, 2006
(Under 37 CFR 1.47)

(65) Prior Publication Data
US 2006/0128959 A1  Jun. 15, 2006

Related U.S. Application Data

(62) Division of application No. 10/847,095, filed on May 17, 2004, now Pat. No. 7,094,931, which is a division of application No. 09/856,769, filed as application No. PCT/EP99/08968 on Nov. 20, 1999, now Pat. No. 6,888,031.

(30) Foreign Application Priority Data

Nov. 30, 1998 (CH) ................................. 2376/98
Dec. 8, 1998 (CH) ................................. 2434/98

(51) Int. Cl.
C07F 9/02 (2006.01)

(52) U.S. Cl. ............................................. 568/8; 568/2
(58) Field of Classification Search ............... 568/8, 568/2
See application file for complete search history.

(56) References Cited

U.S. PATENT DOCUMENTS

| | | | |
|---|---|---|---|
| 4,298,738 A * | 11/1981 | Lechtken et al. | 546/22 |
| 4,522,693 A | 6/1985 | Henne et al. | 204/159.15 |
| 4,737,593 A | 4/1988 | Ellrich et al. | 568/15 |
| 4,792,632 A | 12/1988 | Ellrich et al. | 568/15 |
| 5,218,009 A * | 6/1993 | Rutsch et al. | 522/16 |
| 5,399,770 A | 3/1995 | Leppard et al. | 568/15 |
| 5,472,992 A | 12/1995 | Leppard et al. | 522/18 |
| 5,534,559 A | 7/1996 | Leppard et al. | 522/64 |
| 5,616,787 A * | 4/1997 | Husler et al. | 562/423 |
| 5,721,292 A * | 2/1998 | Leppard et al. | 522/64 |
| 5,767,169 A * | 6/1998 | Leppard et al. | 522/64 |
| 5,965,776 A | 10/1999 | Leppard et al. | 568/15 |
| 6,399,805 B2 | 6/2002 | Wolf et al. | 556/405 |
| 6,579,663 B2 | 6/2003 | Wolf et al. | 430/281.1 |
| 6,888,031 B1 * | 5/2005 | Leppard et al. | 568/14 |

FOREIGN PATENT DOCUMENTS

| | | |
|---|---|---|
| CA | 1117691 | 2/1982 |
| CA | 1193785 | 9/1985 |
| EP | 0040721 | 12/1981 |
| GB | 2259704 | 3/1993 |
| WO | 96/07662 | 3/1996 |

OTHER PUBLICATIONS

Veits et al., Synthesis and Properties of Acyltrialkylphosphines, Zhurnal Obshchei Khimi, 1990, 60 (9) 2028-2036, Abstract.*
S. Banerjee et al., Angew. Makromol. Chem. vol. 199, pp. 1-6, (1992).
Derwent Abstr. 91349 D/50 for EP 0040721 (1981).
C. P. Casey, Journal of Organic Chemistry, vol. 55, No. 4, (1990), pp. 1394-1396.
Chemical Abstract 112:199231 for Journal of Polymer Materials, vol. 6 (2), pp. 135-138, Rahman et al, (1989).
Henderson et al., J. Amer. Chem. Soc., vol. 85, (1962), pp. 2462-2466.
K. Sasse, Houben-Weyl, 12/1, pp. 55-58 (1963).
Issleib et al., Chem. Ber., vol. 92, (1959), pp. 3183-3189.
Chem. Abstr. 54:6504c for Issleib et al., Chem. Ber., vol. 92, (1959), pp. 3183-3189.
Issleib et al., Chem. Ber., vol. 92, (1959), pp. 1118-1126.
Chem. Abstr. 53:17023c, for Issleib et al., Chem. Ber., vol. 92, (1959), pp. 1118-1126.

* cited by examiner

Primary Examiner—Thurman Page
Assistant Examiner—Chukwuma Nwaonicha
(74) Attorney, Agent, or Firm—Joseph C. Suhadolnik

(57) ABSTRACT

A description is given of processes for the preparation of mono- and bisacylphosphines and of mono- and bisacylphosphine oxides and mono- and bisacylphosphine sulfides, which comprises first reacting organic P-monohalogenophosphines or P,P-dihalogenophosphines, or mixtures thereof, with an alkali metal or magnesium in combination with lithium, where appropriate in the presence of a catalyst, and then carrying out the reaction with acid halides and, in the case of the process for the preparation of oxides, carrying out an oxidation step and, in the case of the preparation of sulfides, reacting the phosphines so obtained with sulfur. It is characteristic, inter alia, that the processes are carried out without isolation of the intermediates.

14 Claims, No Drawings

PROCESS FOR THE PREPARATION OF ACYLPHOSPHINES, ACYL OXIDES AND ACYL SULFIDES

This application is a divisional of U.S. application Ser. No. 10/847,095 May 17, 2004, now U.S. Pat. No. 7,094,931, hereby incorporated in its entirety by reference, which is a divisional of U.S. application Ser. No. 09/856,769 filed on Jan. 14, 2002, now U.S. Pat. No. 6,888,031 which is the National Stage of International Application No. PCT/EP99/08968 filed Nov. 20, 1999.

The present invention relates to a process for the preparation of acylphosphines, acyl oxides and acyl sulfides without isolation of the intermediates.

Mono- and bisacylphosphines are known in the state of the art as intermediates which are obtained when preparing mono- and bisacylphosphine oxide or mono- and bisacylphosphine sulfide compounds. These oxides and sulfides find diverse applications as reactive initiators in the light-induced polymerisation of ethylenically unsaturated compounds. This is documented in a plurality of patents, inter alia in U.S. Pat. Nos. 4,298,738, 4,737,593, 4,792,632, 5,218,009, 5,399,770, 5,472,992 or 5,534,559.

U.S. Pat. No. 4,298,738 discloses the preparation of monoacylphosphine oxides via reaction of diorganylphosphine chloride with an alcohol and subsequent reaction of the reaction product with an acid halide. In EP 40721, monoacylphosphines are obtained from the reaction of acid halides with lithium diorganylphosphine, diorganylphosphine or diorganyltrialkylsilylphosphine, which are obtained via reaction with butyl lithium.

In Angew. Makromol. Chem. 199 (1992), 1–6, S. Banerjee et al. describe the preparation of poly(terephthaloylphosphine) via reaction of dilithium phenylphosphine with terephthaloyl chloride.

U.S. Pat. No. 5,472,992, inter alia, carries out the preparation of bisacylphosphine oxide photoinitiators via reaction of the phosphine with the corresponding acid chloride in the presence of a base with subsequent oxidation of the bisacylphosphine formed.

As the technology of the mono- and bisacylphosphine oxides is becoming increasingly important owing to the excellent photoinitiator properties of these compounds, there is also a need for highly practicable processes involving as little elaboration as possible for the preparation of the required intermediates, especially of the corresponding mono- and bisacylphosphines, but also of the oxide and sulfide end products.

A process has now been found by which it is possible to circumvent the use of the phosphine educts ($R_2$—PH, R—$PH_2$) which are undesirable because of their volatility, bad smell, toxicity and susceptibility to air and fire.

This invention relates both to a one-pot process for the preparation of mono- and bisacylphosphines and to a one-pot process for the preparation of mono- and bisacylphosphine oxides or mono- and bisacylphosphine sulfides, where the starting material may be the monohalogenophosphines or P,P-dihalogenophosphines, which are less volatile, less toxic and less susceptible to air.

A process has been found for the preparation of acylphosphines of formula I

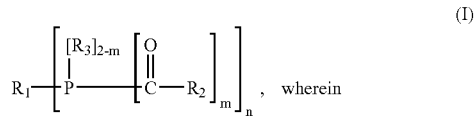

wherein n and m are each independently of the other 1 or 2;

$R_1$, if n=1, is
$C_1$–$C_{18}$alkyl, $C_2$–$C_{18}$alkyl which is interrupted by one or several non-successive O atoms;
phenyl-substituted $C_1$–$C_4$alkyl, $C_2$–$C_8$alkenyl, phenyl, naphthyl, biphenyl, $C_5$–$C_{12}$cycloalkyl or a 5- or 6-membered O—, S— or N-containing heterocyclic ring, the radicals phenyl, naphthyl, biphenyl, $C_5$–$C_{12}$cycloalkyl or the 5- or 6-membered O—, S— or N-containing heterocyclic ring being unsubstituted or substituted by one to five halogen, $C_1$–$C_8$alkyl, $C_1$–$C_8$-alkylthio and/or $C_1$–$C_8$alkoxy;

$R_1$, if n=2, is
$C_1$–$C_{18}$alkylene, $C_2$–$C_{18}$alkylene which is interrupted by one or several non-successive O atoms; or $R_1$ is $C_1$–$C_6$alkylene which is substituted by $C_1$–$C_4$alkoxy, phenyl, $C_1$–$C_4$alkylphenyl, phenyl-$C_1$–$C_4$alkyl or $C_1$–$C_4$alkoxyphenyl; or $R_1$ is phenylene or xylylene, which radicals are unsubstituted or substituted by one to three $C_1$–$C_4$alkyl and/or $C_1$–$C_4$alkoxy, or $R_1$ is a

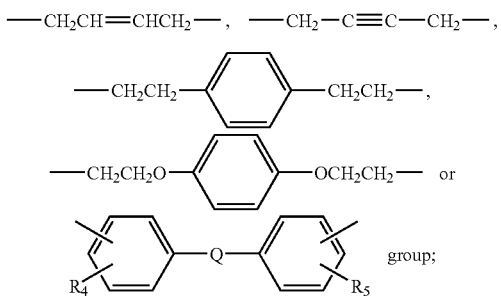

group;

$R_2$ is $C_1$–$C_{18}$alkyl, $C_3$–$C_{12}$cycloalkyl, $C_2$–$C_{18}$alkenyl, phenyl, naphthyl, biphenyl or a 5- or 6-membered O—, S— or N-containing heterocyclic ring, the radicals phenyl, naphthyl, biphenyl or 5- or 6-membered O—, S— or N-containing heterocyclic ring being unsubstituted or substituted by one to four $C_1$–$C_8$alkyl, $C_1$–$C_8$alkoxy, $C_1$–$C_8$alkylthio and/or halogen;

$R_3$ is $C_1$–$C_{18}$alkyl, $C_2$–$C_{18}$alkyl which is interrupted by one or several non-successive O atoms; phenyl-substituted $C_1$–$C_4$alkyl, $C_2$–$C_8$alkenyl, phenyl, naphthyl, biphenyl, $C_5$–$C_{12}$-cycloalkyl or a 5- or 6-membered O—, S— or N-containing heterocyclic ring, the radicals phenyl, naphthyl, biphenyl, $C_5$–$C_{12}$cycloalkyl or the 5- or 6-membered O—, S— or N-containing heterocyclic ring being unsubstituted or substituted by one to five halogen, $C_1$–$C_8$alkyl, $C_1$–$C_8$alkylthio and/or $C_1$–$C_8$alkoxy;

Q is a single bond, $CR_6R_7$, —O— or —S—;

$R_4$ and $R_5$ are each independently of the other hydrogen, $C_1$–$C_4$alkyl or $C_1$–$C_4$alkoxy;

$R_6$ and $R_7$ are each independently of the other hydrogen or $C_1$–$C_4$alkyl; by (1) reacting organic phosphorus halides of formula II

wherein $R_1$, $R_3$, n and m have the meaning cited above, and Y is Br or Cl, with an alkali metal or with magnesium in combination with lithium, or with mixtures thereof, where appropriate in the presence of a catalyst, and (2) subsequent reaction with m add halides of formula III

wherein $R_2$, Y and m have the meaning cited above; which process is carried out without isolation of the intermediates.

In another of its aspects, this invention relates to a process for the preparation of acylphosphine oxides and acylphosphine sulfides of formula IV

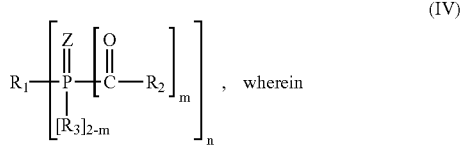

$R_1$, $R_2$, $R_3$, n and m have the meaning cited in claim 1, and Z is O or S, by (1) reacting organic phosphorus halides of formula II

wherein $R_1$, $R_3$, Y, n and m have the meaning cited in claim 1, with an alkali metal or with magnesium in combination with lithium, or with mixtures thereof, where appropriate in the presence of a catalyst, and (2) subsequent reaction with m acid halides of formula III

wherein $R_2$, m and Y have the meaning cited in claim 1, and (3) oxidation or reaction with sulfur of the acylphosphine of formula I

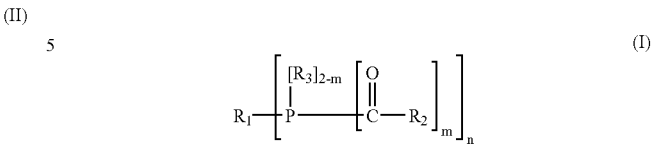

which is obtained by the reaction (2), wherein $R_1$, $R_2$, $R_3$, m and n have the meaning cited in claim 1, which process is carried out without isolation of the intermediates.

$C_1$–$C_{18}$Alkyl is linear or branched and is, for example, $C_1$–$C_{12}$-, $C_1$–$C_8$-, $C_1$–$C_8$- or $C_1$–$C_4$alkyl. Examples are methyl, ethyl, propyl, isopropyl, n-butyl, sec-butyl, isobutyl, tert-butyl, pentyl, hexyl, heptyl, 2,4,4-trimethylpentyl, 2-ethylhexyl, octyl, nonyl, decyl, undecyl, dodecyl, tetradecyl, pentadecyl, hexadecyl, heptadecyl or octadecyl.

$C_1$–$C_{12}$-, $C_1$–$C_8$- and $C_1$–$C_4$Alkyl are also linear or branched and have, for example, the meanings cited above up to the corresponding number of carbon atoms.

$C_2$–$C_{18}$Alkyl, which is interrupted once or several times by non-successive —O—, is interrupted, for example, 1–9, e.g. 1–7, 1–5, 1–3 or 1 or 2, times by —O—, the O atoms always being interrupted by at least one methylene group. The alkyl groups may be linear or branched. The structural units obtained are thus, for example, —$CH_2$—O—$CH_3$, —$CH_2CH_2$—O—$CH_2CH_3$, —[$CH_2CH_2O$]$_y$—$CH_3$, where y=1–8, —($CH_2CH_2O$)$_7CH_2CH_3$, —$CH_2$—$CH(CH_3)$—O—$CH_2$—$CH_2CH_3$ or —$CH_2$—$CH(CH_3)$—O—$CH_2$—$CH_3$.

Phenyl-substituted $C_1$–$C_4$alkyl is typically benzyl, phenylethyl, α-methylbenzyl, phenylbutyl or α,α-dimethylbenzyl, preferably benzyl.

$C_2$–$C_{18}$Alkenyl radicals may be mono- or polyunsaturated, linear or branched and are, for example, allyl, methallyl, 1,1-dimethylallyl, propenyl, butenyl, pentadienyl, hexenyl or octenyl, preferably allyl. $R_2$ defined as $C_2$–$C_{18}$alkenyl is typically $C_2$–$C_8$-, $C_2$–$C_6$-, preferably $C_2$–$C_4$alkenyl.

$C_5$–$C_{12}$Cycloalkyl is, for example, cyclopentyl, cyclohexyl, cyclooctyl, cyclododecyl, preferably cyclopentyl and cyclohexyl, more preferably cyclohexyl. $C_3$–$C_{12}$Cycloalkyl is additionally e.g. cyclopropyl.

$C_1$–$C_8$Alkoxy is linear or branched radicals and is typically methoxy, ethoxy, propoxy, isopropoxy, n-butyloxy, sec-butyloxy, isobutyloxy, tert-butyloxy, pentyloxy, hexyloxy, heptyloxy, 2,4,4-trimethylpentyloxy, 2-ethylhexyloxy or octyloxy, preferably methoxy, ethoxy, propoxy, isopropoxy, n-butyloxy, sec-butyloxy, isobutyloxy, tert-butyloxy, most preferably methoxy.

Halogen is fluoro, chloro, bromo and iodo, preferably chloro and bromo, most preferably chloro.

Examples of O—, S— or N-containing 5- or 6-membered heterocyclic rings are furyl, thienyl, pyrrolyl, oxinyl, dioxinyl or pyridyl. The cited heterocyclic radicals may be substituted by one to five, e.g. by one or two, linear or branched $C_1$–$C_8$alkyl, halogen and/or $C_1$–$C_8$alkoxy. Examples of such compounds are dimethylpyridyl, dimethylpyrrolyl or methylfuryl.

Substituted phenyl, naphthyl or biphenyl is substituted by one to five, e.g. by one, two, three or four, preferably by one or two, for example linear or branched $C_1$–$C_8$alkyl, linear or branched $C_1$–$C_8$alkoxy or by halogen.

Preferred substituents for phenyl, naphthyl and biphenyl are $C_1$–$C_4$alkyl, preferably methyl, $C_1$–$C_4$alkoxy, more preferably methoxy, and chloro. Particularly preferred substituents are, for example, 2,4,6-trimethylphenyl, 2,6-dichlorophenyl, 2,6-dimethylphenyl or 2,6-dimethoxyphenyl.

$R_2$ is, for example, phenyl, preferably 2,4,6-trimethylphenyl, 2,6-dimethylphenyl or 2,6-di-methoxyphenyl, most preferably 2,4,6-trimethylphenyl.

$R_1$ and $R_3$ are preferably unsubstituted phenyl or $C_1$–$C_4$alkyl-substituted phenyl, most preferably phenyl.

$R_1$ defined as $C_1$–$C_{18}$alkylene is linear or branched alkylene, such as methylene, ethylene, propylene, isopropylene, n-butylene, sec-butylene, isobutylene, tert-butylene, pentylene, hexylene, heptylene, octylene, nonylene, decylene, dodecylene, tetradecylene, heptadecylene or octadecylene. $R_1$ is preferably $C_1$–$C_{12}$alkylene, e.g. ethylene, decylene,

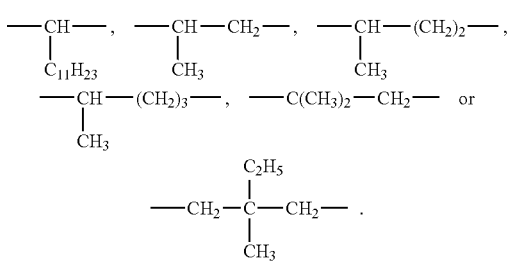

If $R_1$ is $C_2$–$C_{18}$alkylene which is interrupted by one or several non-successive O atoms, then structural units such as —$CH_2$—O—$CH_2$—, —$CH_2CH_2$—O—$CH_2CH_2$—, —[$CH_2CH_2O$]$_y$— are obtained, where y=1–9, —($CH_2CH_2O$)$_7CH_2CH_2$— or —$CH_2$—$CH(CH_3)$—O—$CH_2$—$CH(CH_3)$—.

If alkylene is interrupted by several O atoms, then these O atoms are always separated from each other by at least one methylene group.

Phenyl-$C_1$–$C_4$alkyl is, for example, benzyl, phenylethyl, α-methylbenzyl or α,α-dimethylbenzyl, preferably benzyl. Phenyl-$C_1$–$C_2$alkyl is particularly preferred.

$C_1$–$C_4$Alkylphenyl is typically tolyl, xylyl, mesityl, ethylphenyl, diethylphenyl, preferably tolyl or mesityl.

$C_1$–$C_4$Alkoxyphenyl is phenyl which is substituted by one to four alkoxy radicals, for example 2,6-dimethoxyphenyl, 2,4-dimethoxyphenyl, methoxyphenyl, ethoxyphenyl, propoxyphenyl or butoxyphenyl.

Phenylene is 1,4-, 1,2- or 1,3-phenylene, preferably 1,4-phenylene.

If phenylene is substituted, it is mono- to tetra-substituted, e.g. mono-, di- or trisubstituted, preferably mono- or disubstituted, at the phenyl ring. Xylylene is o-, m- or p-xylylene:

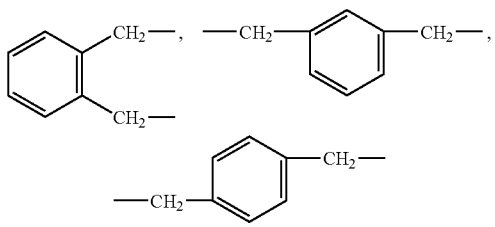

and is, for example, mono- to tetrasubstituted, e.g. mono-, di- or trisubstituted, preferably mono- or disubstituted, at the phenyl ring.

Within the scope of the present description and claims, "and/or" shall mean that not only one of the defined alternatives (substituents) may be present, but that also several different ones of the defined alternatives (substituents) may be present together, i.e. mixtures of different alternatives (substituents).

Within the scope of the present description and claims, "at least" shall be defined as "one" or "more than one", for example one or two or three, preferably one or two.

In the novel process for the preparation of mono- and bisacylphosphines, an organic phosphorus halide (II) is first reacted with an alkali metal or with magnesium in combination with lithium or with mixtures of these metals, the metallised phosphine (IIa) being formed via different intermediary steps:

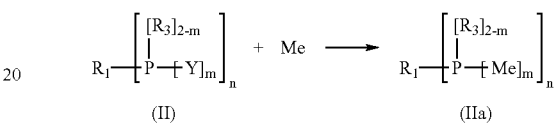

$R_1$, $R_3$, m and n have the meaning cited above, Me is an alkali metal or magnesium or mixtures thereof.

Suitable metals are, for example, lithium, sodium or potassium. It is also possible to use mixtures of these metals in the process of this invention. Magnesium in combination with lithium and/or potassium and/or sodium is also suitable. If lithium, sodium or potassium are used, then it is useful to employ from 4 to 6 atom equivalents of the alkali metal for the preparation of bisacylphosphines, and 2 to 3 atom equivalents of the alkali metal for the preparation of monoacylphosphines. If the reaction is carried out using a mixture of magnesium with one or several alkali metals, then z atom equivalents of magnesium are used and 4 to 6, or 2 or 3, minus z/2 atom equivalents of the alkali metal(s) are added. "z" is a value from 0.5–3.5. If the reaction is carried out using magnesium or sodium in combination with lithium, then the reaction solution is first only charged with magnesium or sodium, the lithium being added later. If magnesium is used, then the magnesium chloride obtained is usefully removed by filtration before the lithium is added.

In the process of this invention the use of lithium, sodium or potassium is preferred.

The reaction is usefully carried out in a solvent. The solvent used may be, in particular, ethers which are liquid at normal pressure and room temperature. Examples thereof are di-methyl ether, diethyl ether, methylpropyl ether, 1,2-dimethoxyethane, bis(2-methoxyethyl)-ether, dioxane or tetrahydrofuran. Tetrahydrofuran is preferably used.

The reaction temperatures are preferably in the range from −20° C. to +120° C., e.g. from 80° C. to 120° C.

Where required, the reaction is carried out with addition of a catalyst. Suitable catalysts are aromatic hydrocarbons, with or without heteroatoms, such as naphthalene, anthracene, phenanthrene, biphenyl, terphenyl, quaterphenyl, triphenylene, trans-1,2-diphenylethene, pyrene, perylene, acenaphthalene, decacyclene, quinoline, N-ethylcarbazole, dibenzothiophene or dibenzofuran.

The reaction (1) is preferably carried out in the presence of a catalyst, preferably naphthalene and biphenyl.

The metallised phosphine (IIa) obtained is further processed in the novel process without isolation.

The metallised phosphine (IIa) obtained as described above is reacted in the next reaction step with an acid halide (III) to the mono- or bisacylphosphine (I):

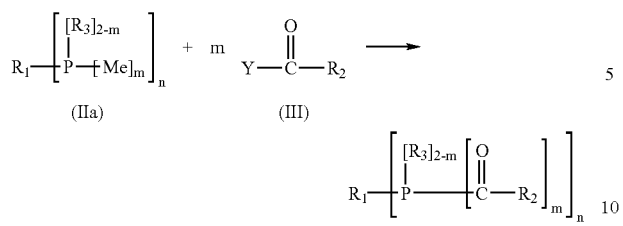

(IIa)    (III)

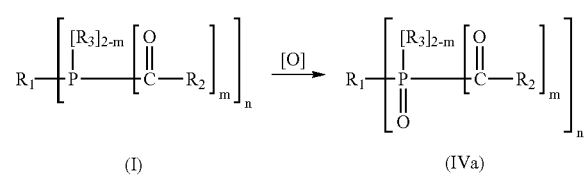

$R_1$, $R_2$, $R_3$, Me, m and n have the meaning cited above. Y is bromo or chloro, preferably chloro.

The solvents used may be, for example, the same as those used above for the first step. However, it is also possible to remove the solvent used in the first step by distillation and to take up the residue in another solvent and then to further process it.

It is preferred to work in the same solvent as in the preceding step, most preferably in tetrahydrofuran.

The reaction temperatures for the reaction with the acid halide are usefully in the range from −20° to +80° C.

In the novel process, the reaction (1) of the organic phosphorus halides (II) is preferably carried out with magnesium in combination with an alkali metal in the temperature range from 80° to 120° C.

In the novel process, the reaction (1) of the organic phosphorus halides (II) with an alkali metal is carried out, for example, in the temperature range from −20° to +120° C.

In the novel process, the reaction (2) of the metallised phosphine with the acid chloride (III) is preferably carried out in the temperature range from −20° to +80° C.

The mono- or bisacylphosphine of formula I can be isolated by the customary technological methods which are known to the skilled person, for example by filtration, evaporation or distillation. Likewise, the customary methods of purification may be used, for example crystallisation, distillation or chromatography.

However, the phosphines can also be reacted without isolation to the corresponding mono- or bisacylphosphine oxides or mono- or bisacylphosphine sulfides.

Depending on the substituents used, isomeric mixtures may be formed by the novel process.

Using the process of this invention it is also possible to prepare mono- and bisacylphosphines together in one reaction step.

By means of the novel process it is furthermore also possible to prepare mixtures of aliphatic and aromatic monoacylphosphines or mixtures of aliphatic and aromatic bisacylphosphines. Mixtures of compounds of formula II, wherein $R_1$ is an aliphatic radical, and of compounds of formula II, wherein $R_1$ is an aromatic radical, are used in this case.

If required, all of the mixtures may be separated by the processes customarily used in the technology or they may be further used as they are.

This invention also relates to a process for the preparation of mono- and bisacylphosphine oxides or mono- and bisacylphosphine sulfides. This process is first carried out as described above and a mono- or bisacylphosphine (I) is prepared. The crude reaction product (I) can then be further processed without purification and an additional reaction step may be carried out without isolation of the phosphine (I) using the solution of the crude product. If required, the solvent may be changed, for example by concentrating the solution containing the mono- or bisacylphosphine and taking up the residue in a new solvent. Of course it is also possible to further react above-described unseparated mixtures of compounds of formula (I) to the corresponding oxide or sulfide.

When preparing the respective oxide (IVa), the oxidation of the phosphine (I) is carried out using the oxidant conventionally used in the technology:

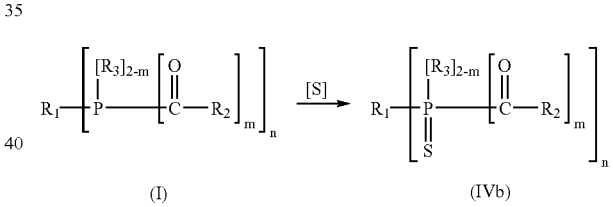

(I)    (IVa)

Suitable oxidants are in particular hydrogen peroxide and organic peroxy compounds, for example peracetic acid or t-butylhydroperoxide, air or pure oxygen.

The oxidation is usefully carried out in solution. Suitable solvents are aromatic hydrocarbons, such as benzene, toluene, m-xylene, p-xylene, ethylbenzene or mesitylene, or aliphatic hydrocarbons, such as alkanes and alkane mixtures, e.g. petroleum ether, hexane or cyclohexane.

During oxidation, the reaction temperature is preferably kept in the range from 0° to 120° C., preferably from 20° and 80° C.

The reaction products (IVa) can be isolated and purified by conventional processing methods known to the skilled person.

The respective sulfide (IVb) is prepared by reaction with sulfur:

$$R_1 \!-\!\left[\!P\genfrac{}{}{0pt}{}{[R_3]_{2-m}}{}\!-\!\left[\genfrac{}{}{0pt}{}{O}{\|}\!-\!C\!-\!R_2\right]_m\right]_n \xrightarrow{[S]} R_1\!-\!\left[\!P\genfrac{}{}{0pt}{}{[R_3]_{2-m}}{\underset{S}{\|}}\!-\!\left[\genfrac{}{}{0pt}{}{O}{\|}\!-\!C\!-\!R_2\right]_m\right]_n$$

(I)    (IVb)

The mono- or bisacylphosphines (I) are in this case reacted in substance or, where appropriate, in a suitable inert organic solvent with an equimolar to 2-fold molar amount of elementary sulfur. Suitable solvents are for example those described for the oxidation reaction. However, it is also possible to use e.g. aliphatic or aromatic ethers, such as dibutyl ether, dioxane, diethylene glycol dimethyl ether or diphenyl ether, in the temperature range from 20° to 250° C., preferably from 60° to 120° C. The resulting mono- or bisacylphosphine sulfide, or its solution, is usefully freed from any remaining elementary sulfur by filtration. After the solvent is removed, the mono- or bisacylphosphine sulfide can be isolated by distillation or recrystallisation in pure form.

As mentioned above, it is also possible to use mixtures of compounds of formula I for the oxidation or reaction to the sulfide. The correspondingly obtained oxide or sulfide mixtures can either be separated by processes customarily used in the technology or may be used as mixtures.

All of the above reactions are usefully carried out with exclusion of air in an inert gas atmosphere, e.g. under nitrogen or argon gas. The respective reaction mixture is usefully also stirred.

The acid halides (III) used as starting materials are known substances, some of which are commercially available, or may be prepared in analogy to known compounds.

The preparation of the phosphorus halides (II) is also described in a great number of publications and can be carried out in analogy to the descriptions provided there. In J. Chem. Soc. (1935), 462 and J. Chem. Soc. (1944), 276, W. Davies discloses for example the preparation of aryl phosphorus chlorides by reaction of arylene with phosphorus trichloride in the presence of aluminium trichloride. According to F. Nief, Tetrahedron 47 (1991) 33, 667 or Th. Knapp, Tetrahedron 40(1984) 4, 76, the Grignard reaction of aryl halides with magnesium and phosphorus trichloride is another possibility. According to S. Metzger, J. Org. Chem. 29 (1964), 627, alkylphosphorus chlorides are accessible in the same manner. In Helv. Chim. Act. 36 (1953), 1314, Th. Weil describes the reaction of aryl halides or alkyl halides with magnesium followed by the reaction with zinc chloride and subsequent reaction with phosphorus trichloride. The reaction of aryl halides with butyl lithium and phosphorus trichloride to the corresponding aryl phosphorus chloride is disclosed by G. Whitesides in JACS 96 (1974), 5398. According to Th. Knapp, Tetrahedron 40 (1984) 4, 765, the reaction of the aryl magnesium halide with bis(dimethylamino)phosphorus chloride followed by the reaction with hydrochloric acid also results in the desired starting material. According to A. Burg, U.S. Pat. No. 2,934,564, the same method may also be used for the preparation of the corresponding alkyl phosphorus chlorides.

It is characteristic of the novel process that the acylphosphines, acylphosphine oxides or acylphosphine sulfides can be prepared without using the phosphine starting materials ($R_2PH$, $RPH_2$) which are usually employed. It is also crucial that the individual processing steps can be carried out directly one after the other without isolating the respective intermediates and purifying them especially.

Mixtures such as those described in the process for the preparation of the corresponding phosphines may also be formed, or may also be specifically produced, in the above-described process for the preparation of mono- or bisacylphosphine oxides or mono- or bisacylphosphine sulfides. Such mixtures can be separated by methods known in the technology or may be further used in the form of mixtures.

In the above-described processes, $R_1$, if n=1, is $C_1$–$C_{12}$alkyl, cyclohexyl, phenyl or biphenyl, the radicals phenyl and biphenyl being unsubstituted or substituted by one to four $C_1$–$C_8$alkyl and/or $C_1$–$C_8$alkoxy;

$R_1$, if n=2, is $C_8$–$C_{10}$alkylene, or

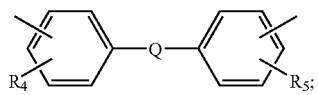

$R_3$ is $C_1$–$C_{12}$alkyl, cyclohexyl, phenyl or biphenyl, the radicals phenyl and biphenyl being unsubstituted or substituted by one to four $C_1$–$C_8$alkyl and/or $C_1$–$C_8$alkoxy;

Q is a single bond or —O—, and $R_4$ and $R_5$ are hydrogen.

Compounds to be highlighted in the above processes are those of formula I, wherein $R_2$ is phenyl which is substituted in 2,6- or 2,4,6-position by $C_1$–$C_4$alkyl and/or $C_1$–$C_4$alkoxy.

Compounds of formula I which are particularly preferably used in the above process are those wherein n is 1.

Y in formula II of the novel process is preferably chloro.

Other preferred compounds of formula I in the above process are those, wherein m is defined as the number two, i.e. bisacylphosphine or bisacylphosphine oxides or bisacylphosphine sulfides.

A preferred process is that, wherein in formula, I, n is 1, m is 1 or 2, $R_1$ is phenyl which is unsubstituted or substituted by $C_1$–$C_4$alkyl or $C_1$–$C_8$alkoxy, or $R_1$ is $C_1$–$C_{12}$alkyl; $R_2$ is phenyl which is substituted by halogen, $C_1$–$C_4$alkoxy or $C_1$–$C_4$alkyl; and $R_3$ is unsubstituted or $C_1$–$C_4$-alkyl-substituted phenyl.

This invention also relates to the compounds and mixtures of compounds obtained by the novel process.

The phosphines which are accessible by the novel process are important educts for the preparation of the corresponding phosphine oxides and phosphine sulfides. The phosphine oxides and phosphine sulfides are used in the art as initiators in photopolymerisation reactions.

The following Examples illustrate the invention in more detail. As in the remaining description and in the patent claims, parts or percentages are by weight, unless otherwise stated.

EXAMPLE 1

Preparation of bis(2,4,6-trimethylbenzoyl)phenylphosphine oxide

Excluding moisture by an argon atmosphere, 7 g of lithium (1.0 mol; 25% excess) are suspended at room temperature in 400 ml of tetrahydrofuran (THF) and this suspension is charged with 1.0 g (0.008 mol) of naphthalene. This mixture is then stirred for 10 minutes at room temperature, resulting in a dark brown to black suspension. With vigorous stirring, a solution of 36.50 g of P,P-dichlorophenylphosphine (98%; 0.20 mol) in 80 ml of THF is added dropwise over 1 hour at 20–25° C. (occasional cooling in an ice bath). With exclusion of moisture and using argon protective gas, the black solution is filtered via a glass frit (G2 porosity) into a sulfonation flask. With stirring and cooling in an ice bath, a solution of 80.4 g of 2,4,6-trimethylbenzoyl chloride (0.44 mol; 10% excess) in 250 ml of THF is added dropwise at room temperature over 1.5 hours and the mixture is then stirred for another 15 minutes at room temperature. The organic phase is completely concentrated by evaporation in a rotary evaporator (the resulting phosphine has a 53.78 ppm shift in the $^{31}$P-NMR spectrum) and the residue is taken up in 200 ml of toluene and heated to 40° C. With vigorous stirring and some cooling with an ice bath, 23 g of 30% hydrogen peroxide (0.20 mol) are added dropwise over 30 minutes and the mixture is then cooled, with stirring, to room temperature. The solution is charged with 40 ml of water and the phases are separated. The organic phase is washed twice with 30 ml each of a 10% sodium hydrogencarbonate solution and then twice with 30 ml each of water. After drying over magnesium sulfate, filtration and complete evaporation of the solvent, 85 g of a yellow oil are obtained which becomes solid after drying for one hour at about 0.1 mbar. This crude product is purified by being slurried in 150 ml of warm petroleum ether/ethyl acetate (9:1), filtering and washing with 30 ml of petroleum ether (40/60), which yields 71.5 g (85.40% yield) of the title product in the form of a yellow solid having a melting point (m.p.) of 131–132° C. and a 7.43 ppm shift in the $^{31}$P-NMR spectrum. Another 14 g of the yellow oil are obtained from the mother liquor by concentrating the solvent completely, which oil is then purified by flash chromatography, yielding another 4.3 g of the title product. The total yield is thus 76.0 g (90.8% yield).

EXAMPLE 2

Preparation of bis(2,6-dimethoxybenzoyl)phenylphosphine oxide

The procedure of Example 1 is repeated, but replacing the 2,4,6-trimethylbenzoyl chloride with 82.25 g of 2,6-dimethoxybenzoyl chloride. The phosphine obtained has a 52.17 ppm shift in the $^{31}$P-NMR spectrum and a melting point of 120–125° C. 20.1 g (64% yield) of the title product are obtained in the form of a yellow powder having a melting point of 155° C. and a $^{31}$P-NMR shift of 6.24 ppm.

EXAMPLE 3

Preparation of bis(2,6-dichlorobenzoyl)phenylphosphine oxide

The procedure of Example 1 is repeated, but replacing the 2,4,6-trimethylbenzoyl chloride with 85.8 g of 2,6-dichlorobenzoyl chloride. The phosphine obtained has a melting point of 117–119° C. 35.0 g (74% yield) of the title product are obtained in the form of a yellowish brown powder. Recrystallisation from acetonitrile yields a yellow solid having a melting point of 194° C.

EXAMPLE 4

Preparation of bis(2,4,6-trimethylbenzoyl)phenylphosphine sulfide

Under an argon atmosphere and with exclusion of moisture, 7 g of lithium (1.0 mol; 25% excess) are suspended at room temperature in 400 ml of tetrahydrofuran (THF) and this suspension is charged with 1.0 g (0.008 mol) of naphthalene. This mixture is then stirred for 10 minutes at room temperature, resulting in a dark brown to black suspension. With vigorous stirring, a solution of 36.50 g of P,P-dichlorophenylphosphine (98%; 0.20 mol) in 80 ml of THF is added dropwise over 1 hour at 20–25° C. (occasional cooling with an ice bath). With exclusion of moisture and using argon protective gas, the black solution is filtered via a glass frit (G2 porosity) into a sulfonation flask. With stirring and cooling with an ice bath, a solution of 80.4 g of 2,4,6-trimethylbenzoyl chloride (0.44 mol; 10% excess) in 250 ml of THF is added dropwise over 1.5 hours at room temperature and the mixture is then stirred for another 15 minutes at room temperature. The organic phase is completely concentrated by evaporation in a rotary evaporator and the residue is taken up in 200 ml of toluene and heated to 40° C. The solution is charged with 3.7 g of sulfur and this mixture is stirred for 6 hours at 60° C. Removal of the solvent yields 39.0 g (89.9% yield) of a yellow oil which is recrystallised from acetonitrile, yielding the title product in the form of a yellow solid having a melting point of 123° C.

EXAMPLE 5

Preparation of bis(2,6-dimethoxybenzoyl)phenylphosphine sulfide

The procedure of Example 4 is repeated, but replacing the 2,4,6-trimethylbenzoyl chloride with 82.25 g of 2,6-dimethoxybenzoyl chloride. The amount of sulfur added is 4.91 g. Removal of the solvent and recrystallisation from 100 ml of ethyl acetate yields 21.0 g (66.0% yield) of the title product in the form of a yellow solid having a melting point of 155° C.

EXAMPLE 6

Preparation of bis(2,4,6-trimethylbenzoyl)-(2,4-dipentoxyphenyl)phosphine oxide

Under an argon atmosphere and with exclusion of moisture, 6.2 g of lithium (0.89 mol; 12% excess) are suspended at room temperature in 400 ml of tetrahydrofuran (THF) and this suspension is charged with 1.0 g (0.008 mol) of naphthalene. This mixture is then stirred for 10 minutes at room temperature, resulting in a dark brown to black suspension. With vigorous stirring, a solution of 74.0 g of 2,4-dipentoxyphenyl-P,P-dichlorophenylphosphine (95%; 0.20 mol) in 50 ml of THF is then added dropwise over 1.5 hours at 20–25° C. (occasional cooling with an ice bath). The resulting mixture is stirred for 6 hours at 50° C. With exclusion of moisture and using argon protective gas, the black solution is filtered via a glass frit (G2 porosity) into a sulfonation flask. With stirring and cooling with an ice bath, a solution of 76.7 g of 2,4,6-trimethylbenzoyl chloride (0.42 mol; 5% excess) in 200 ml of THF is then added dropwise over 1.5 hours at room temperature and the mixture is then stirred for another 15 minutes at room temperature. The organic phase is completely concentrated by evaporation in a rotary evaporator (the resulting phosphine has a $^{31}$P-NMR shift of 42.7 ppm) and the residue is taken up in 300 ml of toluene and heated to 40° C. With vigorous stirring and some cooling with an ice bath, 23 g of 30% hydrogen peroxide (0.20 mol) are added dropwise over 30 minutes and the mixture is then stirred for another 2.5 hours at 50° C. until the reaction is complete. The reaction mixture is then allowed to cool, with stirring, to room temperature. The yellow reaction mixture is filtered over diatomaceous earth. The solution is then charged with 40 ml water and the phases are separated. The organic phase is washed twice with 50 ml each of a 10% sodium hydrogencarbonate solution and then twice with 50 ml each of water. Drying over magnesium sulfate, filtration and complete evaporation of the solvent in a rotary evaporator yields 120 g of a yellow oil. This crude product is dissolved, with heating, in 200 ml of hexane and is then allowed to cool first to 20° C. and is then cooled to 0° C., the title product crystallising out in the form of a yellow solid. The product is filtered cold and washed twice with 20 ml each of cold hexane, and the resulting solid is dried in a vacuum drying oven for 12 hours at 40° C. and 155 mm Hg, yielding 70.0 g (59.3% yield) of the solid having a melting point of 91° C. and a $^{31}$P-NMR shift of 14.48 ppm. Another 16.0 g of the title product are obtained from the mother liquor by concentrating the solvent completely and subsequent purification via column chromatography.

EXAMPLE 7

Preparation of bis(2,6-dimethoxybenzoyl)-2,4-dipentoxyphenylphosphine oxide

The procedure of Example 6 is repeated, but replacing the 2,4,6-trimethylbenzoyl chloride with 72.0 g of 2,6-dimethoxybenzoyl chloride, resulting in 94.0 g (73.4% yield) of a yellow resin. This crude product is purified via column chromatography, resulting in 56.8 g of the resin having a melting point of 68° C.

EXAMPLE 8

Preparation of bis(2,4,6-trimethylbenzoyl)ethylphosphine oxide

Under an argon atmosphere and with exclusion of moisture, 2.67 g of lithium (0.38 mol) are suspended at room temperature in 150 ml of tetrahydrofuran (THF) and this suspension is charged with 0.38 g (0.003 mol) of naphthalene. This mixture is then stirred for 10 minutes at room temperature, resulting in a dark brown to black suspension. With vigorous stirring, a solution of 10.0 g of P,P-dichloroethylphosphine (0.076 mol) in 20 ml THF is added dropwise over 1 hour at 20–25° C. (occasional cooling with an ice bath). The resulting mixture is stirred for 18 hours at room temperature. With exclusion of moisture and using argon protective gas, the black solution is filtered via a glass frit (G2 porosity) into a sulfonation flask. With stirring and cooling with an ice bath, a solution of 27.87 g of 2,4,6-trimethylbenzoyl chloride (0.15 mol) in 100 ml THF is added over 1.5 hours at room temperature and the mixture is then stirred for another 15 minutes at room temperature. The organic phase is completely concentrated at reduced pressure and the residue is taken up in 100 ml of toluene, 8.7 g of 30% hydrogen peroxide then being added dropwise at 50–60° C. over 30 minutes. To complete the reaction, the mixture is stirred for another hour at 60° C. The reaction mixture is then allowed to cool to room temperature and the phases are separated. The organic phase is washed twice with 50 ml each of a 10% sodium hydrogencarbonate solution and then twice with 50 ml each of water. Drying over magnesium sulfate, filtration and complete evaporation of the solvent in a rotary evaporator yields 28.0 g (97.6%) of a yellow oil which is recrystallised from ethyl acetate, yielding the title product having a melting point of 142° C.

EXAMPLES 9–12

The compounds of the Examples 9–12 are prepared in analogy to the method described in Example 8, using the corresponding educts. The compounds and their physical data ($^{31}$P-NMR shifts in [ppm] and/or melting point in [° C.]) are compiled in the following Table 1.

TABLE 1

| Ex. | R | x = 0 physical data | x = 1 physical data |
|-----|-----|-----|-----|
| 9 | isobutyl | 50.06 ppm | 85–86° C.; 28.76 ppm |
| 10 | octyl | 53.68 ppm | yellow viscous oil; 28.73 ppm |
| 11 | 2-ethylhexyl | 48.82 ppm | yellow viscous oil; 29.59 ppm |
| 12 | propen-1-yl | — | cis-form: 147° C. trans-form: yellow viscous oil |

EXAMPLE 13

Preparation of 2,4,6-trimethylbenzoylditolylphosphine oxide (Isomeric Mixture Consisting of di-ortho, di-para and ortho-para-product)

Under argon and with exclusion of moisture, 4.6 g of chopped sodium (0.20 mol) are placed at room temperature in 100 ml of tetrahydrofuran. Stirring slowly, 24.9 g (0.10 mol) of ditolylphosphine chloride (isomeric mixture of di-ortho, di-para and ortho-para) are added dropwise at 20–25° C. After stirring for 12 h, the red solution is filtered via a glass frit (G2 porosity) into a sulfonation flask with exclusion of moisture and using argon as protective gas. With stirring and cooling, 19.0 g (0.105 mol; 5% excess) of 2,4,6-trimethylbenzoyl chloride are added dropwise over 30 minutes at room temperature. After stirring for another 2 hours, the brownish-red reaction suspension is poured on water and extracted with toluene. The organic phase is dried over magnesium sulfate, filtered and concentrated by evaporation in a rotary evaporator (Rotavap). The resulting phosphine has a 23.24 ppm shift in the $^{31}$P-NMR spectrum. The residue is taken up in 100 ml of toluene and charged with 11.5 g (0.10 mol) of hydrogen peroxide (30%). The reaction is complete after stirring for 2 hours at a temperature from 50–60° C. The reaction emulsion is poured on water and washed with an aqueous saturated sodium hydrogencarbonate solution and then dried over magnesium sulfate and filtered. The filtrate is concentrated by evaporation in a Rotavap. The residue is purified over silica gel and dried under high vacuum, yielding 33.8 g (90% of theory) of the title compound in the form of a yellow viscous oil. The $^{31}$P-NMR shift is 14.54 ppm.

EXAMPLE 14

Preparation of 2,4,6-trimethylbenzoyldiphenylphosphine oxide

Under argon and with exclusion of moisture, 2.76 g of lithium (0.40 mol) are suspended at room temperature in 100 ml of THF and this suspension is charged with 0.10 g (0.00078 mol) of naphthalene. This mixture is then stirred for 10 minutes at room temperature. With occasional cooling and vigorous stirring, 45.2 g (0.0 mol) of P-chlorodiphenyl phosphine are added dropwise to the dark brown suspension at 10–25° C. After stirring for 4 hours, the red solution is filtered via a glass frit (G2 porosity) into a sulfonation flask with exclusion of moisture and using argon as protective gas. 38.0 g (0.2 mol) of 2,4,6-trimethylbenzoyl chloride are added dropwise, with stirring and cooling, at 10–20° C. over 1 hour and the mixture is then stirred for another 30 minutes. The organic phase is concentrated by evaporation in a Rotavap and the residue is taken up in 100 ml of toluene and charged, with vigorous stirring at a temperature from 50–60° C., with 23.0 g (0.20 mol) of hydrogen peroxide (30%). The reaction is complete after stirring for 30 minutes. The reaction emulsion is poured on water and washed with an aqueous saturated sodium hydrogencarbonate solution and then dried over magnesium sulfate and filtered. The filtrate is concentrated by evaporation in a Rotavap. The residue is crystallised from petroleum ether/ethyl acetate and dried in a vacuum drying oven at 40° C., yielding 55.0 g (79% of theory) of the title compound in the form of a yellow powder having a melting point of 89–90° C.

EXAMPLE 15

Preparation of 2,6-dimethoxybenzoyldiphenylphosphine oxide 2,6-Dimethoxybenzoyl(diphenyl)phosphine oxide is prepared in analogy to the method described in Example 14, but replacing the 2,4,6-trimethylbenzoyl chloride with 2,6-dimethoxybenzoyl chloride. The $^{31}$P-NMR shift of the phosphine is 20.17 ppm. This gives 25 g of 2,6-dimethoxybenzoyl(diphenyl)phosphine oxide having a melting point of 120–121° C. and a $^{31}$P-NMR shift of 10.19 ppm. This corresponds to a yield of 68% of theory.

EXAMPLE 16

Preparation of a mixture of 2,4,6-trimethylbenzoyldiphenylphosphine oxide and bis(2,4,6-trimethylbenzoyl)phenylphosphine oxide Under argon and with exclusion of moisture, 2.1 g of lithium (0.30 mol) and 0.1 g of naphthalene are placed at room temperature in 100 ml of THF. With stirring, 2.7 g (0.015 mol) of dichlorophenylphosphine, followed by 9.9 g (0.045 mol) of chlorodiphenylphosphine, are added dropwise at 20–25° C. After stirring for 12 hours, the red solution is filtered via a glass frit (G2 porosity) into a sulfonation flask with exclusion of moisture and using argon as protective gas. With stirring and cooling, 13.7 g (0.075 mol) of 2,4,6-trimethylbenzoyl chloride are added dropwise over 30 minutes at room temperature. After stirring for another 2 hours, the brownish-red reaction suspension is concentrated by evaporation in a rotary evaporator. The residue is taken up in 100 ml of toluene and charged with 17 g (0.15 mol) of 30% hydrogen peroxide. The reaction is complete after stirring for 2 hours at a temperature from 50–60° C. The reaction emulsion is poured on water and washed with an aqueous saturated sodium hydrogencarbonate solution and is then dried over magnesium sulfate and filtered. The filtrate is concentrated by evaporation in a rotary evaporator. The residue is purified over silica gel and dried under high vacuum, yielding 10.3 g (47% of theory) of the title compounds in a ratio of 3:1 in the form of a yellow, viscous oil.

EXAMPLE 17

Preparation of a mixture of bis(2,4,6-trimethylbenzoyl)-1,1-dimethylethylphosphine oxide and bis(2,4,6-trimethylbenzoyl)phenylphosphine oxide Excluding moisture by an argon protective gas atmosphere, 3.5 g of lithium (0.504 mol) and 0.1 9 of naphthalene are placed in 100 ml of THF at room temperature. With stirring, 11.3 g (0.063 mol) of dichlorophenylphosphine, followed by 10 g (0.063 mol) of dichloro-tert-butyl phosphine, are added dropwise at 20–25° C. After stirring for 72 hours, the red solution is filtered via a glass frit (G2 porosity) into a sulfonation flask with exclusion of moisture and using argon as protective gas. With stirring and cooling, 23.0 g (0.126 mol) of 2,4,6-trimethylbenzoyl chloride are added dropwise over 30 minutes at room temperature. After stirring for another 2 hours, the brownish-red reaction suspension is concentrated by evaporation in a rotary evaporator. The residue is taken up in 100 ml of toluene and charged with 28.6 g (0.252 mol) of 30% hydrogen peroxide. The reaction is complete after stirring for 2 hours at a temperature from 50–60° C. The reaction emulsion is poured on water and washed with an aqueous saturated sodium hydrogencarbonate solution and is then dried over magnesium sulfate and filtered. The filtrate is then concentrated by evaporation in a rotary evaporator. The residue is purified over silica gel and dried under a high vacuum, yielding 7.6 g (15% of theory) of the title compounds in a ratio of 65:35 in the form of a yellow, viscous oil.

The invention claimed is:
1. A process for the preparation of acyl phosphines of formula I

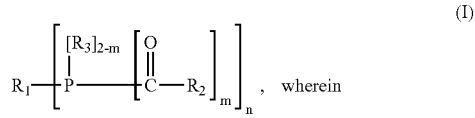

n and m are each independently of the other 1 or 2;
$R_1$, if n=1, is
$C_1$–$C_{18}$alkyl, $C_2$–$C_{18}$alkyl which is interrupted by one or several non-successive O atoms;
phenyl-substituted $C_1$–$C_4$alkyl, $C_2$–$C_8$alkenyl, phenyl, naphthyl, biphenyl, $C_5$–$C_{12}$cycloalkyl or a 5- or 6-membered O—, S— or N-containing heterocyclic ring, the radicals phenyl, naphthyl, biphenyl, $C_5$–$C_{12}$cycloalkyl or the 5- or 6-membered O—, S— or N-containing heterocyclic ring being unsubstituted or substituted by one to five halogen, $C_1$–$C_8$alkyl, $C_1$–$C_8$alkylthio and/or $C_1$–$C_8$alkoxy;
$R_1$, if n=2, is
$C_1$–$C_{18}$alkylene, $C_2$–$C_{18}$alkylene which is interrupted by one or several non-successive O atoms; or
$R_1$ is $C_1$–$C_6$alkylene which is substituted by $C_1$–$C_4$alkoxy, phenyl, $C_1$–$C_4$alkylphenyl, phenyl-$C_1$–$C_4$alkyl or $C_1$–$C_4$alkoxyphenyl; or $R_1$ is phenylene or xylylene, which radicals are unsubstituted or substituted by one to three $C_1$–$C_4$alkyl and/or $C_1$–$C_4$alkoxy, or $R_1$ is a

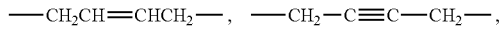

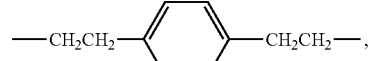

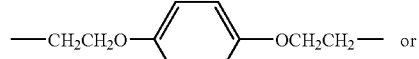

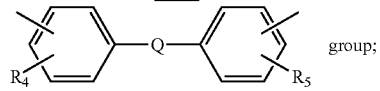

group;

$R_2$ is $C_1$–$C_{18}$alkyl, $C_3$–$C_{12}$cycloalkyl, $C_2$–$C_{18}$alkenyl, phenyl, naphthyl, biphenyl or a 5- or 6-membered O—, S— or N-containing heterocyclic ring, the radicals phenyl, naphthyl, biphenyl or 5- or 6-membered O—, S— or N-containing heterocyclic ring being unsubstituted or substituted by one to four $C_1$–$C_8$alkyl, $C_1$–$C_8$alkoxy, $C_1$–$C_8$alkylthio and/or halogen;
$R_3$ is $C_1$–$C_{18}$alkyl, $C_2$–$C_{18}$alkyl which is interrupted by one or several non-successive O atoms;
phenyl-substituted $C_1$–$C_4$alkyl, $C_2$–$C_8$alkenyl, phenyl, naphthyl, biphenyl, $C_5$–$C_{12}$cycloalkyl or a 5- or 6-membered O—, S— or N-containing heterocyclic ring, the radicals phenyl, naphthyl, biphenyl, $C_5$–$C_{12}$cycloalkyl or the 5- or 6-membered O—, S— or N-containing heterocyclic ring being unsubstituted or substituted by one to five halogen, $C_1$–$C_8$alkyl, $C_1$–$C_8$alkylthio and/or $C_1$–$C_8$alkoxy;

Q is a single bond, $CR_6R_7$, —O— or —S—;

$R_4$ and $R_5$ are each independently of the other hydrogen, $C_1$–$C_4$alkyl or $C_1$–$C_4$alkoxy;

$R_6$ and $R_7$ are each independently of the other hydrogen or $C_1$–$C_4$alkyl;

by (1) reacting organic phosphorus halides of formula II

  (II)

wherein $R_1$, $R_3$, n and m have the meaning cited above, and Y is Br or Cl, with an alkali metal or with magnesium in combination with lithium, or with mixtures thereof, optionally in the presence of a catalyst, and (2) subsequent reaction with m acid equivalents of halides of formula III

  (III)

wherein $R_2$, Y and m have the meaning cited above;

which process is carried out without isolation of the intermediates.

2. A process according to claim 1, wherein $R_1$, if n=1, is $C_1$–$C_{12}$alkyl, cyclohexyl, phenyl or biphenyl, the radicals phenyl and biphenyl being unsubstituted or substituted by one to four $C_1$–$C_8$alkyl and/or $C_1$–$C_8$alkoxy;

$R_1$, if n=2, is $C_6$–$C_{10}$alkylene, or

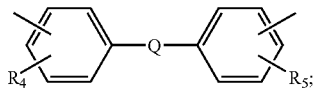

$R_3$ is $C_1$–$C_{12}$alkyl, cyclohexyl, phenyl or biphenyl, the groups phenyl and biphenyl being unsubstituted or substituted by one to four $C_1$–$C_8$alkyl and/or $C_1$–$C_8$alkoxy;

Q is a single bond or —O—, and $R_4$ and $R_5$ are hydrogen.

3. A process according to claim 1, wherein $R_2$ is phenyl which is substituted in 2,6- or 2,4,6-position by $C_1$–$C_4$alkyl and/or $C_1$–$C_4$alkoxy.

4. A process according to claim 1, wherein n is 1.

5. A process according to claim 1, wherein Y in formula II is chloro.

6. A process according to claim 1, wherein the reaction (1) is carried out using lithium, sodium or potassium.

7. A process according to claim 6, wherein from 4 to 6 atom equivalents of the alkali metal are used for the preparation of compounds of formula I, wherein m is 2, and 2 to 3 atom equivalents of the alkali metal are used for the preparation of compounds of formula I, wherein m is 1.

8. A process according to claim 1, wherein Y in the compounds of formula III is chloro.

9. A process according to claim 1, which comprises carrying out the reaction (1) in the presence of a catalyst.

10. A process according to claim 1, which comprises carrying out the reaction (1) of the organic phosphorus halides (II) with an alkali metal in the temperature range from −20° to +120° C.

11. A process according to claim 1, which comprises carrying out the reaction (1) of the organic phosphorus halides (II) with magnesium in combination with an alkali metal in the temperature range from 80° to 120° C.

12. A process according to claim 1, wherein the reaction (2) of the metallised phosphine with the acid chloride (III) is carried out at −20° to +80° C.

13. A process according to claim 1, wherein the reaction steps (1) and (2) are carried out in the same solvent.

14. A process according to claim 1, wherein, in formula I, n is 1, m is 1 or 2, $R_1$ is phenyl which is unsubstituted or substituted by $C_1$–$C_4$alkyl or $C_1$–$C_8$alkoxy, or $R_1$ is $C_1$–$C_{12}$alkyl; $R_2$ is phenyl which is substituted by halogen, $C_1$–$C_4$alkoxy or $C_1$–$C_4$alkyl; and $R_3$ is unsubstituted or $C_1$–$C_4$alkyl-substituted phenyl.

* * * * *